(12) United States Patent
Solomon et al.

(10) Patent No.: US 6,286,368 B1
(45) Date of Patent: Sep. 11, 2001

(54) SELF-IMMERSING WETTING BALANCE

(75) Inventors: Harvey Donald Solomon; Ronald Edward Delair, both of Schenectady; Leslie Homer String, Johnstown, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/663,636

(22) Filed: Sep. 18, 2000

(51) Int. Cl.$^7$ ........................................................ G01L 9/10
(52) U.S. Cl. ................................................ 73/437; 73/774
(58) Field of Search ............................. 73/774, 776, 760, 73/763, 862.381, 437, 436

(56) References Cited

U.S. PATENT DOCUMENTS

| | | | |
|---|---|---|---|
| 4,197,273 | * | 4/1980 | Dusserre et al. ........................ 73/437 |
| 5,102,621 | * | 4/1992 | Sara ..................................... 420/470 |
| 5,262,022 | * | 11/1993 | Tench et al. ............................ 205/791 |

OTHER PUBLICATIONS

"Principles of Soldering and Brazing", by Humpston et al., over year published, pp. 191–193.
"Wettability at High Temperatures", by Eustathopoulos et al., 1999, pp. 130–134, 145–147.
"Simultaneous Measurement of Contact Angles and work of Adhesion in Metal–Cermic Systems by Immersion–Emersion Technique", by Rivollet et al., 1990, 7 pages.

* cited by examiner

*Primary Examiner*—Max Noori
(74) *Attorney, Agent, or Firm*—Noreen C. Johnson; Douglas E. Stoner

(57) ABSTRACT

A wetting balance includes a load cell for suspending a specimen above a crucible containing a molten braze pool. A lift supports the crucible for vertical lifting thereof to effect an immersion cycle of the specimen in the pool. A controller operates the lift and determines first contact with the pool by measuring force changes thereat and produces a measured force log during the immersion cycle. In operation, the lift is operated for a predetermined time following first contact for immersing the specimen to a predetermined depth in the pool.

15 Claims, 3 Drawing Sheets

SELF-IMMERSING WETTING BALANCE

BACKGROUND OF THE INVENTION

The present invention relates generally to brazing, and, more specifically, to wetting balances for measuring wetting force during brazing.

Soldering and brazing are related processes used for bonding together metal components. Soldering occurs at relatively low temperature for typically bonding together copper or brass parts, and brazing requires substantially higher temperatures for bonding together high strength materials including stainless steel and various superalloys typically used in manufacturing gas turbine engines, including nickel based superalloys.

Various brazing materials are tailored to the specific material of the parts being brazed for effecting high strength joints therewith. However, an effective braze joint requires wetting of the molten braze material with the surface of the part so that upon cooling and solidification thereof a strong integral metallurgical bond is created.

Wetting of solder with copper parts generally occurs practically instantaneously. Wetting of typical braze materials with corresponding parts may occur practically instantaneously or may require a considerable time exceeding tens of seconds, and in some cases wetting may not occur at all irrespective of the amount of time permitted therefor.

The wetting time of a particular braze material with a corresponding part requiring brazing is a primary parameter in the brazing process. Whether brazing is effected manually or automatically, sufficient time must be provided to ensure proper wetting for obtaining a full strength braze joint.

Wetting performance of solder and braze materials is typically evaluated in commercially available wetting balances. A typical wetting balance suspends a specimen from a weighing device such as a micro-balance or load cell, and a crucible containing molten solder or braze material is lifted for immersing the bottom portion of the specimen into a molten solder or braze pool to a preferred depth. The molten solder or braze pool applies a force to the specimen which varies depending upon the degree of wetting or non-wetting thereof.

In wetting, the molten pool adheres to the specimen and creates a rising positive meniscus having a corresponding wetting angle less than 90°. In non-wetting, the molten pool does not adhere to the specimen and effects an opposite depression or negative meniscus with a correspondingly different wetting angle greater than 90°.

By accurately measuring the force applied to the specimen during immersion in the molten pool, the wetting angle and wetting force may be analytically derived. Accordingly, the wetting performance of various solder or braze materials may be quantitatively evaluated.

However, one form of a wetting balance uses a precision micro-balance beam for suspending the specimen and measuring the applied force from the molten pool. The balance beam measures force precisely, yet is relatively slow in operation for balancing the applied force. And, the specimen correspondingly changes immersion depth as the balance beam equilibrates.

Another type of wetting balance includes a conventional load cell from which the specimen is suspended. The load cell, although not as precise as the balance beam, measures applied force substantially instantaneously. And, the specimen is maintained at a fixed elevation which does not affect the immersion depth in the molten pool.

In both wetting balance types, the specimen is partially immersed in the molten pool, and the immersion depth must be accurately determined for use in accurately determining the wetting angle and wetting force. Immersion depth is typically separately measured by optical observation.

Accordingly, it is desired to provide a wetting balance having improved accuracy and ease of use in measuring applied force and determining corresponding wetting force.

BRIEF SUMMARY OF THE INVENTION

A wetting balance includes a load cell for suspending a specimen above a crucible containing a molten braze pool. A lift supports the crucible for vertical lifting thereof to effect an immersion cycle of the specimen in the pool. A controller operates the lift and determines first contact with the pool by measuring force changes thereat and produces a measured force log during the immersion cycle. In operation, the lift is operated for a predetermined time following first contact for immersing the specimen to a predetermined depth in the pool.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
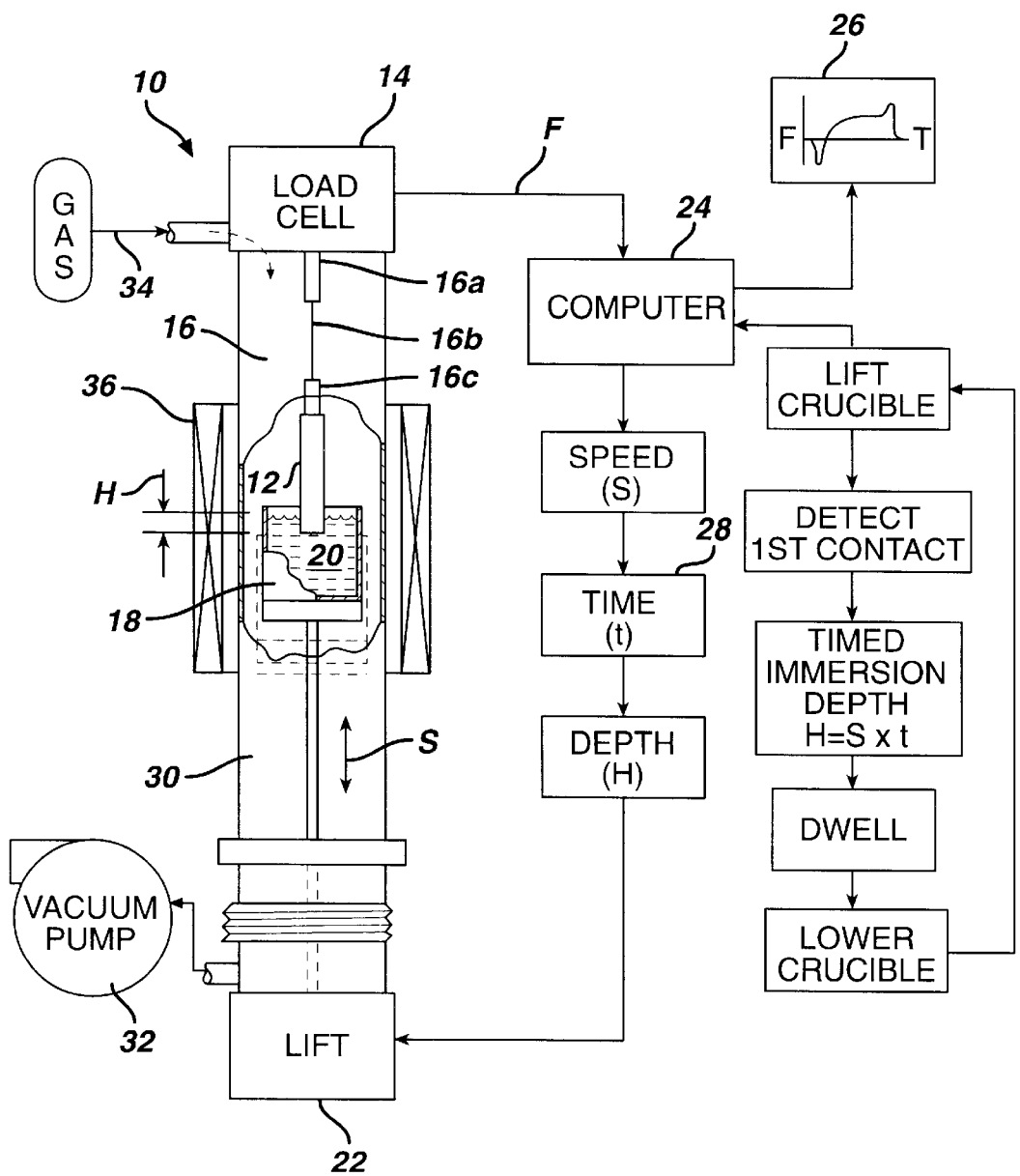
FIG. 1 Ha schematic, elevational view of a wetting balance in accordance with an exemplary embodiment of the present invention, including a flowchart method of operation.

Illustrated schematically in FIG. 1 is a wetting apparatus or balance 10 in accordance with an exemplary embodiment of the present invention. The balance is an assembly of components configured for measuring force on a suitable test specimen 12 during brazing.

The balance includes means in the form of a load cell 14 which includes a holder or sling 16 for suspending the specimen 12 below the load cell and measuring vertical force thereon. The load cell may have any conventional configuration and preferably includes a tare feature for offsetting the entire suspended weight of the specimen when not subject to externally applied force. The output of the load cell is an electrical signal representative of external force applied to the suspended specimen.

A crucible 18 is disposed below the load cell 14 in vertical alignment with the specimen for containing a molten braze liquid or pool 20 for use in conducting a wetting balance test with the corresponding specimen. The specimen 12 may have any desired material composition, such as stainless steel or various nickel based superalloys typically used in gas turbine engines.

The braze pool 20 may have any suitable material composition for use in testing braze performance with the corresponding specimen 13. In this way, the wetting performance of the specific combination of specimen and braze materials may be evaluated for ensuring effective braze joints of parts requiring brazing in any desirable manufacturing application.

The crucible 18 may have any suitable configuration and is typically formed of any inert material for withstanding the high temperature required for maintaining the braze material in its molten state. For example, the crucible may be formed of a suitable ceramic such as $Al_2O_3$.

Means in the form of an elevator or lift 22 are provided for supporting the crucible below the specimen for vertical lifting of the crucible in conducting an immersion-emersion cycle for a wetting balance test.

The lift 22 may have any conventional form including an electrical motor driving a screw shaft having a platform at a distal end supporting the crucible. In this way, the vertical elevation of the crucible may be accurately controlled as it is raised or lowered during the test cycle.

Means in the form of an electrical control 24 are operatively joined to the load cell 14 by a suitable electrical line for obtaining an electrical signal corresponding with the measured force from the load cell. The controller 24 is also operatively joined to the lift 22 through a suitable electrical line to the motor thereof for controlling elevation of the lift platform and the crucible 18 resting thereatop.

In a preferred embodiment, the controller 24 is in the form of a digitally programmable computer which may be configured in suitable software for controlling the entire wetting balance test cycle and data generated therein.

More specifically, the controller 24 is configured in a programmed cycle for automatically operating the lift to elevate the crucible 18 from an initial retracted or resting position suitably below the specimen. The crucible is lifted vertically upwardly for achieving first contact between the specimen and molten pool at which a corresponding first contact force is measured by the load cell 15. The lift is also operated to immerse the specimen into the braze pool to a predetermined depth H in a predetermined time t following detection of the first contact force for self-immersing the specimen in the pool.

At the predetermined depth, the lift is stopped for maintaining the immersion depth constant for a predetermined dwell time or interval as required for observing wetting between the specimen and braze pool, if wetting occurs at all.

The lift 22 is then operated in reverse for retracting or withdrawing its platform and the crucible supported thereon for withdrawing the specimen from the pool. And, during this immersion-emersion test cycle, the output from the load cell 14 is received by the controller 24 for producing or recording a history log 26 of the force F on the specimen due to the molten braze material as measured by the load cell over the elapsed time of the desired cycle.

The wetting balance 10 illustrated in FIG. 1 is operated by initially suspending the specimen 12 of desired material composition from the load cell. The desired braze material being tested is then suitably melted to form the molten pool 20 contained in the crucible 18. The crucible is supported by the lift 22 at any suitable rest position directly below the specimen 12 for positioning the braze pool directly below the specimen.

The controller 24 is suitably programmed for automatically effecting the desired immersion-emersion test cycle by initially operating the lift for lifting the crucible and pool therein upwardly toward the specimen for controlled immersion of the specimen therein.

In accordance with the present invention, the load cell 14 is used for detecting first contact of the specimen upon immersion into the braze pool. Prior to immersion, the load cell 14 measures no external applied force and produces an output signal representative of either the starting weight of the specimen, or a zero weight due to subtracting the corresponding tare weight of the specimen supported in the load cell.

Upon first contact of the specimen in the braze pool, an initial first contact force is detected or measured by the load cell and communicated to the controller 24. Any suitable value of detected change in force due to first contact of the specimen and pool may then be used to effect the predetermined immersion depth H desired.

The controller 24 merely stops operation of the lift 22 at a predetermined time t following detection of first contact corresponding with the desired immersion depth H. By simply stopping operation of the lift 22 after a suitable time period from detection of first contact, the specimen may be precisely immersed at the desired depth H without the need for optical control of that immersion depth, or control thereof by other means. The wetting balance is thusly configured for self-immersing the specimen in the pool automatically and with high precision.

Upon achieving the desired immersion depth, the lift 22 is turned off for then maintaining a substantially constant immersion depth for a desired dwell time or interval for evaluating whether or not wetting of the braze pool is effected with the immersed specimen.

Following the desired dwell period, the controller operates the lift 22 for retracting or lowering the crucible 18 to correspondingly withdraw the specimen from the braze pool to complete the testing cycle.

During the entire cycle, the load cell transmits the measured force signal to the controller 24, and the controller suitably records or logs the measured force over the time of the testing cycle to produce a corresponding data log 26. The data log may have any suitable form such as the force-time graph illustrated generally in FIG. 1, and in more detail in FIG. 2.

Figure 2:
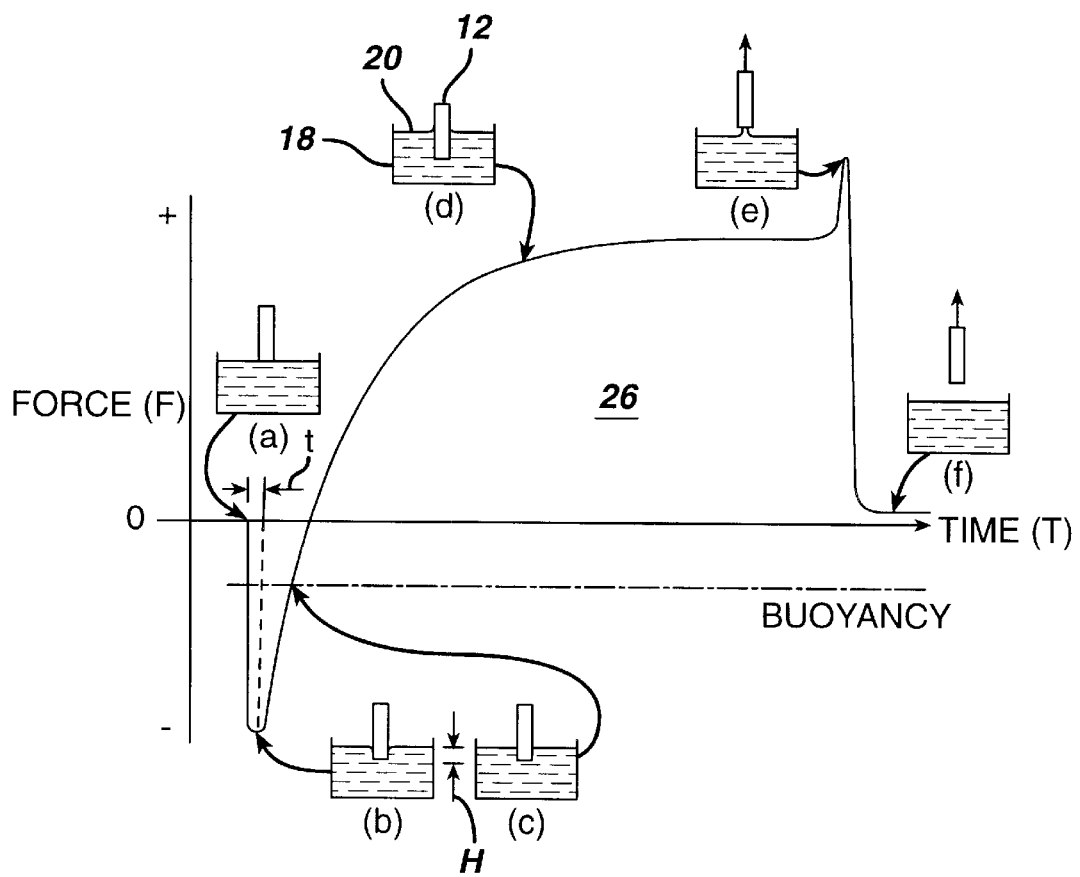
FIG. 2 is a log graph of an exemplary measured force from the load cell illustrated in FIG. 1 over an immersion-emersion cycle of the specimen including wetting thereof.

The test log 26 illustrated in FIG. 2 is an example of measured force from the load cell 14 for a specimen immersed in a braze pool in which wetting occurs over a suitable elapsed time. The log is highlighted with six corresponding conditions of the specimen being immersed in the braze pool designated (a)–(f).

More specifically, the test starts with the crucible disposed below the specimen and being raised until first contact of the specimen with the braze pool at condition (a). Prior to first contact, the load cell produces an indication of zero applied force on the specimen.

Lifting of the crucible correspondingly causes the specimen to be immersed in the braze pool to the maximum or predetermined immersion depth H occurring at condition (b). As the specimen is submerged in the braze pool, a buoyancy force is developed on the specimen which pushes upwardly on the specimen for developing a negative value of applied force. The maximum or peak negative force applied prior to wetting occurs immediately upon immersion to the maximum depth at condition (b).

In the event that the materials of the specimen and braze pool are compatible for developing braze wetting, wetting is initiated over time following maximum immersion, and includes the two conditions (c) and (d).

As wetting occurs, the measured force increases from its negative peak until it equals that negative force due to buoyancy at condition (c). As wetting continues, the measured force F increases further and becomes positive. The positive measured force corresponds with wetting which pulls the stationary specimen in the downward direction into the pool. The measured force continues to rise positive as wetting continues until it reaches a substantially steady state or constant positive value beginning at condition (d).

Following the steady state measured force, the crucible is lowered which introduces a positive peak force at condition (e) as the specimen is withdrawn from the braze pool. The measured force drops to substantially zero value at condition (f) after removal of the specimen from the pool, and may have a slightly positive value due to any remaining braze material adhering to the specimen.

Wetting force is a term of art and is developed by the balance of surface tension acting on a liquid as it wets or does not wet a liquid surface. Wetting force is a function of wetting angle which is the angle defined by the balance of surface tension developed between the specimen and surrounding vapor, the surface tension between the molten liquid and the specimen, and the surface tension between the molten liquid and the vapor.

Figure 3:
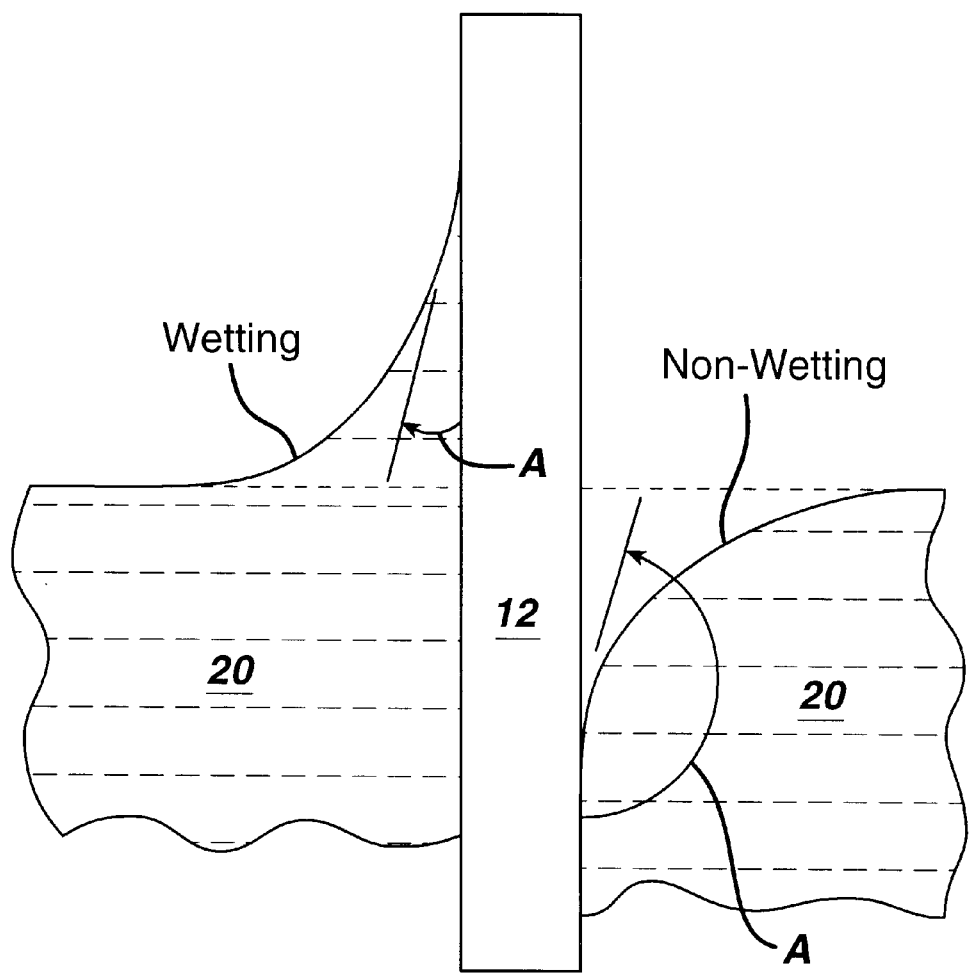
FIG. 3 is an enlarged view of the specimen illustrated in FIG. 1 illustrating braze wetting on the left side thereof, and non-wetting braze on the right side thereof, and the corresponding meniscus and wetting angle representative of each condition.

FIG. 3 illustrates schematically on the left side, wetting of the braze pool 20 with the specimen 12 which creates a positive meniscus due to capillary rise, with a corresponding wetting angle A less than 90°. On the right side of FIG. 3, the braze pool is non-wetting with the specimen and creates a negative meniscus with a corresponding wetting angle A greater than 90°.

Accordingly, the wetting force on a specimen may be derived in different manners by measuring applied external force on the specimen from the braze pool and calculating wetting force. Or, optical observations of the meniscus may be used for determining wetting force.

One derivation of wetting force FW is represented by the following equation:

$$FW = (9.807/(2(W+b))) \times (F + \rho WbH)$$

In this equation, W is the width of the rectangular specimen beam, b is its thickness, H is the depth of immersion, p is the density of the braze liquid, and F is the measured force from the load cell having an initial value of zero prior to immersion. Force data from the measurement log 26 illustrated in FIG. 2 may be applied to this equation for producing corresponding values of the wetting force for further analysis as desired.

A particular advantage of the wetting balance illustrated in FIG. 1 is its ability to automatically self-immerse the specimen 12 to the predetermined immersion depth H following self-detection of first contact with the braze pool. The specimen is then quickly and accurately immersed to the selected depth, and that depth is accurately maintained constant for the desired duration of the test prior to retraction of the crucible.

The use of the load cell 14 is preferred over a conventional micro-balance for quickly and accurately detecting first contact from which the desired immersion depth is referenced. In a preferred embodiment, first contact is detected by measuring change in force from the load cell which exceeds a pre-selected threshold force value suitably above electronic noise and preferably less than about 1% of the maximum load rating capability of the load cell. Preferably, the threshold force is about 0.1% of the maximum load rating capability of the load cell, and corresponds with about 0.05 gram which is readily detectable by the load cell.

Upon detection of first contact at this substantially small threshold value, the lift 22 continues to operate preferably at a substantially constant speed S to lift the crucible at that speed so that the predetermined immersion depth H may be obtained by simple clock timing of the lift for the desired time corresponding with the desired immersion depth.

By using the controller 24 in the form of a digitally programmable computer, the computer may include an internal timing circuit or clock 28 suitably configured with software for stopping immersion lifting operation of the lift 22 at the desired predetermined time following detection of the first contact for immersing the specimen to the desired predetermined depth H. For a desired immersion depth H, and with a given constant lift speed S, the corresponding immersion time t is simply the quotient thereof.

Depending upon the specific material compositions of the specimen and braze, wetting may occur almost instantaneously upon immersion, or may occur after several seconds, or may not occur at all in a non-wetting combination. The immersion-emersion test cycle must be sufficiently long for correspondingly long wetting or non-wetting applications, or may be relatively short for fast wetting material combinations. In either case, it is desirable to accurately measure the applied force on the specimen due to immersion in the braze pool for accurately deriving the wetting force.

The load cell 14 preferably has any suitable conventional configuration for measuring force on the specimen substantially instantaneously, as opposed to the slower acting microbalances typically used in wetting balances. The time response of the load cell should be suitably fast for accurately measuring force preferably at 0.1 second intervals or faster.

In this way, the lift 22 may operate at relatively fast elevating speeds for promptly immersing the specimen to the required depth and immediately recording the applied loads from the braze pool. In a preferred embodiment, the lift speed S is greater than about 10 mm/min and may be up to about 600 mm/min, or higher if desired.

In order to protect the load cell 14 during relative movement between the suspended specimen and the crucible, the sling 16 is preferably flexible yet permits effective immersion of the specimen in the molten braze.

More specifically, the sling 16 illustrated in FIG. 1 preferably includes a straight rod 16a threaded at its top end for being threadingly joined to a threaded stem on the load cell. A flexible wire 16b is suitably suspended from the lower end of the rod, and may be formed of a suitable material such as platinum or stainless steel.

A specimen holder 16c is suitably suspended from the lower end of the wire by welding or mechanical attachment. And, the specimen 12 is then suitably attached to the lower end of the holder by screwing, clamping, or welding.

The flexible wire may buckle under excessive upward force on the specimen during immersion to protect the delicate load cell from overloading. For example, if the braze is not sufficiently molten, impact of the specimen therewith will buckle the wire and protect the load cell.

However, the specimen holder is provided with sufficient mass to ensure that the specimen is forced into the braze when sufficiently molten. The holder acts like an anchor under gravity to immerse the attached specimen into the molten braze notwithstanding the flexibility of the wire, which wire is weighted by the holder to remain taught.

The rod, wire, holder, and specimen are preferably coaxially aligned with each other to maintain a vertically straight loadpath through the wire to the load cell for accurately measuring the small changes in force as the specimen undergoes the immersion cycle.

As the immersion speed increases, the operating time t to achieve the desired predetermined depth H decreases. As illustrated in FIG. 2, the measured force F from the load cell, as the specimen is rapidly immersed in the pool, increases with a steep slope to the peak or maximum negative measured force at condition (b) at which the maximum immersion depth is first reached within the corresponding travel time t.

An accurate value of the peak negative force F is measured by the load cell 14 and may be used in a conventional manner for deriving both surface tension and wetting force at condition (b).

In FIG. 2, wetting may occur between conditions (b) and (d) in the course of several seconds. Or, such wetting may occur substantially instantaneously in less than a second or fraction of a second. Or, wetting may not occur at all irrespective of the amount of testing or dwell time following condition (b).

Fast wetting braze-specimen combinations may be accurately tested notwithstanding the speed of immersion, which may occur in less than a second. The self-immersing specimen quickly and accurately reaches the desired predetermined immersion depth H while the load cell 14 quickly and accurately measures the applied force which is conveniently stored and displayed by the computer 24 in any desired manner.

Brazing occurs at temperatures substantially greater than those typically found in common soldering. And, a commercially available wetting balance configured for testing solder wetting lacks the capability for suitably testing brazes.

Accordingly, the wetting balance 10 illustrated in FIG. 1 preferably also includes an isolation chamber 30 in the preferred form of a quartz tube sealingly surrounding the crucible 18 and the specimen 12 for isolation thereof from the surrounding air environment. The chamber 30 is suitably sealingly joined to the load cell 14 and lift 22 with O-rings or other seals as desired.

The chamber may be joined to the lift 22 using a suitable steel expansion bellows to provide sealing while permitting lifting motion of the supporting crucible. A quartz rod preferably extends between the lift and crucible to uncouple heat transfer therebetween.

A suitable vacuum pump 32 may be operatively joined to the isolation chamber 30 for evacuating air therefrom. For example, the vacuum pump 32 may be operated to evacuate the chamber 30 of air which is substantially free or devoid of air and oxygen to less than about 50 part-per-billion (ppb), for example. Undesirable oxidation during the testing process may be reduced by substantially eliminating oxygen in any conventional manner including titanium getter foils.

The isolation chamber 30 may then be filled with a suitable inert gas 34 provided from a suitable gas supply operatively joined to the chamber. A suitable inert gas is argon, and may also include hydrogen.

In order to maintain a suitable elevated temperature of the molten braze pool 20 during the test, a heating furnace 36 suitably surrounds the crucible 18, preferably outside the chamber 30 for heating the pool to maintain a desired temperature thereof. The furnace 36 may take any conventional form such as infrared radiant electrical furnace for achieving molten temperatures up to about 1125° C.

Soldering typically occurs at solder temperatures less than about 400° C., with brazing requiring temperatures substantially greater.

High temperature braze testing requires corresponding low vacuum in the isolation chamber, with the air environment being replaced by an inert gas for reducing undesirable oxidation during testing. For higher temperature braze testing in the exemplary range of 1500° C.–2500° C., greater initial vacuums up to about $10^{-6}$ torr are desirable. And, inert gas in combination with hydrogen at greater than about 3%, or even pure hydrogen, is preferably used in the testing apparatus.

Higher temperature operation of the wetting balance may be achieved using higher temperature resistance furnaces, or a radiant energy furnace using quartz heat lamps and parabolic reflectors, or a radio frequency (RF) furnace with a susceptor.

By suitably heating the braze pool 20 in an environment of inert gas substantially devoid of air and oxygen during the immersion testing cycle, accurate braze wetting performance may be tested.

By logging the measured force over time during the testing cycle for determining the specific configuration of the wetting performance log 26 illustrated in FIG. 2, accurate evaluation of the wetting performance for specific combinations of specimen and braze material may be obtained.

For example, the wetting force attributable to a specific combination of specimen and braze materials may be readily determined using the exemplary equation described above in which the geometric parameters of the specimen are given, the density of the braze pool is given, the immersion depth H is specified and automatically effected in the manner disclosed above, with the measured force represented by the log illustrated in FIG. 2 being introduced into the equation for determining a corresponding wetting force over the duration of the test.

The measured force data contained in the log 26 illustrated in FIG. 2 may also be used in any conventional manner in evaluating various parameters associated with braze wetting, including wetting angle and surface tension, for example.

The self-immersion feature of the present invention may be readily incorporated in various forms of wetting balances to advantage. Immersion depth may be accurately effected and maintained by timed operation of the lifting apparatus following the detection of first specimen-to-pool contact. The specimen may be immersed to a specific depth which is then maintained constant for the duration of the test. Alternatively, the immersion depth may be varied as desired during testing for any suitable advantage. In either case, accurate determination of the actual immersion depth is readily known by the time interval following first contact during which the crucible is elevated at constant speed.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which we claim:

1. A wetting balance for measuring force on a specimen during brazing, comprising:

a load cell including a sling for suspending said specimen and measuring a vertical force thereon;

a crucible disposed below said load cell for containing a molten braze pool;

a lift supporting said crucible for vertical lifting thereof;

a controller operatively joined to said load cell for obtaining measured force therefrom including first contact force of said specimen entering said pool, and operatively joined to said lift for controlling elevation of said crucible; and said controller being configured for elevating said crucible in a cycle to immerse said specimen into said braze pool to a predetermined depth in a predetermined time following said first contact force; to maintain said immersion depth for a time interval; and then to withdraw said specimen from said pool while producing a log of measured force on said specimen over time of said cycle.

2. A method of using said balance according to claim 1 comprising:

positioning said crucible with said braze pool therein below said specimen suspended from said load cell;

lifting said crucible to immerse said specimen in said pool;

detecting first contact of said specimen upon immersion in said pool by measuring change in force on said specimen;

stopping said crucible lifting at said predetermined time following detection of said first contact to immerse said specimen to said predetermined depth;

maintaining said immersion depth for said time interval;

lowering said crucible to withdraw said specimen from said pool; and logging said force over time during said cycle.

3. A method according to claim 2 wherein said first contact is detected by measuring change in said force exceeding a threshold force less than 1% of maximum load rating of said load cell.

4. A method according to claim 3 wherein said lifting is effected at a substantially constant speed.

5. A balance according to claim 1 wherein load cell is configured for measuring said force on said specimen substantially instantaneously.

6. A balance according to claim 5 further comprising:

an isolation chamber sealingly surrounding said crucible and specimen for isolation thereof from a surrounding air environment; and a furnace surrounding said crucible for heating said pool to maintain molten temperature thereof.

7. A balance according to claim 6 wherein said controller comprises a digitally programmable computer including a timing circuit configured for stopping immersion lifting operation of said lift at said predetermined time following detection of said first contact to immerse said specimen to said predetermined depth.

8. A balance according to claim 7 wherein said isolation chamber is substantially devoid of air and oxygen, and includes an inert gas.

9. A balance according to claim 5 wherein said sling comprises:

a rod suspended from said load cell;

a flexible wire suspended from said rod; and a specimen holder suspended from said wire to suspend said specimen.

10. A method of measuring force on a suspended specimen during brazing comprising:

lifting a crucible containing a molten braze pool to immerse said specimen therein;

detecting first contact of said specimen upon immersion in said pool by measuring force change on said specimen;

stopping said crucible lifting at a predetermined time following detection of said first contact to immerse said specimen to a predetermined immersion depth;

maintaining said immersion depth for a dwell time interval;

lowering said crucible to withdraw said specimen from said pool; and measuring force on said specimen during said lifting-to-lowering immersion cycle.

11. A method according to claim 10 wherein said crucible is lifted at a substantially constant speed from said first contact until said stopping thereof.

12. A method according to claim 11 wherein said force on said specimen is measured substantially instantaneously.

13. A method according to claim 12 further comprising heating said pool in an environment of inert gas substantially devoid of air and oxygen during said immersion cycle.

14. A method according to claim 13 further comprising logging said measured force over time during said immersion cycle.

15. A method according to claim 14 further comprising determining wetting force for said specimen in said pool from said immersion depth and said measured force.

* * * * *